Figure 1:
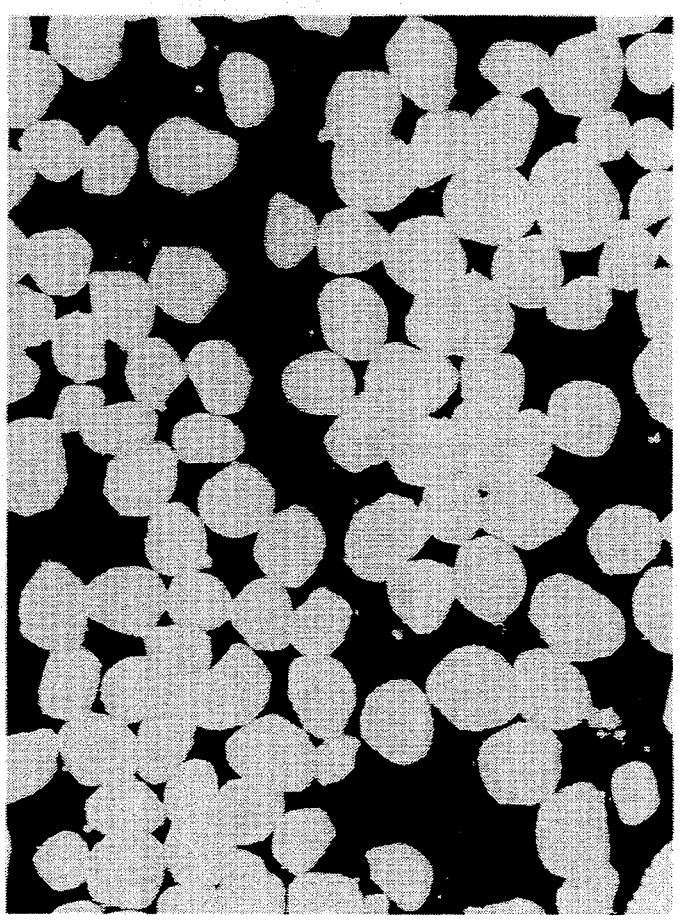

United States Patent [19]

Slangen et al.

[11] Patent Number: 5,355,590
[45] Date of Patent: Oct. 18, 1994

[54] PROCESS FOR THE DRYING AND GRANULATION OF ASPARTAME

[75] Inventors: Hubertus J. M. Slangen, Stein; Mathieu H. M. Mertens, Sittard, both of Netherlands

[73] Assignee: Holland Sweetener Company V.o.F., Maastricht, Netherlands

[21] Appl. No.: 914,239

[22] Filed: Jul. 17, 1992

[30] Foreign Application Priority Data

Sep. 2, 1991 [NL] Netherlands ............... 9101477

[51] Int. Cl.$^5$ .............................. F26B 7/00
[52] U.S. Cl. ........................ 34/385; 34/181; 34/443; 118/20
[58] Field of Search .......... 34/12, 22, 60, 132, 34/134, 179, 181; 118/19, 20, 303

[56] References Cited

U.S. PATENT DOCUMENTS

| | | | |
|---|---|---|---|
| 4,875,435 | 10/1989 | Jan et al. | 34/181 |
| 4,967,688 | 11/1990 | Funakoshi et al. | 118/303 |
| 5,271,163 | 12/1993 | Pikus et al. | 34/181 |

FOREIGN PATENT DOCUMENTS

| | | |
|---|---|---|
| 0256517 | 2/1988 | European Pat. Off. |
| 1127815 | 4/1962 | Fed. Rep. of Germany |
| 8900819 | 2/1989 | PCT Int'l Appl. |

*Primary Examiner*—Denise Gromada
*Attorney, Agent, or Firm*—Cushman, Darby & Cushman

[57] ABSTRACT

The invention relates to a process for the drying and granulation of aspartame through the thermal treatment of a wet mass of aspartame crystals using a hot carrier gas, characterized in that a wet mass of aspartame crystals is supplied, in a continuous process, to a high-speed paddle dryer fitted with a jacket heated to a temperature of 80°–190° C. and with paddles, mounted on a central shaft with a controllable speed of rotation, at an adjustable distance from and angle to the jacket, which are positioned so that the required particle size of the granules is realized, the speed of rotation being chosen so that the Froude number is higher than 1, and the supplied product is treated in the paddle dryer for 15–600 seconds, with the simultaneous presence of a carrier gas having an inlet temperature of 100°–200° C., and the granular product obtained is discharged from the paddle dryer and, if necessary, dried further—in a manner known per se—in one or more drying steps in other drying equipment. With the use of high-speed paddle dryer aspartame with good microbiological properties is very easily obtained.

18 Claims, 1 Drawing Sheet

PROCESS FOR THE DRYING AND GRANULATION OF ASPARTAME

The invention relates to a process for the drying and granulation of aspartame through the thermal treatment of a wet mass of aspartame crystals using a hot carrier gas.

Such a process for the production of dry aspartame granules is known from EP-A-256515, which describes that granules are obtained by successively separating off wet aspartame crystals from a slurry of aspartame, producing granules with diameters of 0.1–10 mm from this wet mass of crystals and finally treating this product using a stream of air with an absolute moisture content of more than 0.015 or less than 0.01 kg/kg, at a temperature of preferably at most 0° C., in for example a fluidized-bed dryer.

This process presents several drawbacks. For example, it requires a relatively sensitive control of the absolute humidity of the drying air. In addition, the drying takes a relatively large amount of time, particularly if the final moisture content of the granules is to be low, i.e. <4%. This has an adverse effect on the cost price of the product. Also, the particle size distribution of the product thus obtained is relatively wide: on the one hand the product contains oversized granules and, on the other, a large amount of fines is formed in the drying step. Consequently, the product obtained is not suitable for sale on the market without an aftertreatment (grinding and/or screening). Moreover, the bulk density is insufficient for various applications.

The aim of the invention now is to provide a process which yields dry granular aspartame with a high bulk density as well as a narrow, controllable, particle size distribution, the production process being simple and taking little time. Moreover, deposition and decomposition problems are virtually absent in this process.

This aim is achieved according to the invention because a wet mass of aspartame crystals is supplied, in a continuous process, to a high-speed paddle dryer fitted with a jacket heated to a temperature of 80°–190° C. and with paddles, mounted on a central shaft with a controllable speed of rotation, at an adjustable distance from and angle to the jacket, which are positioned so that the required particle size of the granules is realized, the speed of rotation being chosen so that the resultant Froude number is higher than 1, and the supplied product is treated in the paddle dryer for 20–600 seconds, with the simultaneous presence of a carrier gas having an inlet temperature of 100°–200° C. and the granular product obtained is discharged from the paddle dryer and, if necessary, dried further—in a manner known per se—in one or more drying steps in other drying equipment.

For the sake of convenience, the dryer used in the essential drying step is referred to as an HSPD (high-speed paddle dryer) in the rest of this application. The speed of rotation, expressed as the Froude number, defined as $\omega^2 r/g$ is higher than 1 and as a rule lower than 500. Preferably, the Froude number is between 20 and 400, in particular between 100 and 300. In $\omega^2 r/g$ $\omega$ is the angular velocity (in rad/s), r is the radius of the dryer (in m) and g is the gravity acceleration (in m/s$^2$).

'Wet mass of crystals' is understood to be crystalline aspartame with a moisture content of, as a rule, 40–70%. 'The amount of moisture' is in this application understood to be the amount in the wet mass of crystals. Hence, % is used in this application throughout as wt.% with respect to the total mass, unless defined otherwise. The wet mass of crystals may be for example a paste, a slurry, a wet cake, lumps, or, optionally, granules with a non-desired particle size distribution.

Even at high carrier gas temperatures, which is surprising, the process according to the invention yields granular aspartame of excellent quality as regards its chemical composition, narrow particle size distribution and high bulk density. As will be shown below, it is with this process possible to vary and/or control the particle size, even within a wide range, without affecting the narrow particle size distribution.

Moreover, the process according to the invention involves no or only a scarcely observable deterioration of the product quality owing to decomposition.

It should be noted that many embodiments for the drying of aspartame have so far been described. However, not one of these resembles the method according to the present invention, neither as regards the process nor the result, as will be dealt with in great detail further on in this introduction to the specification. EP-A-0362706 describes an example of the drying of aspartame with the aid of hot air of between 80° and 200° C. This describes how crystalline aspartame, obtained by cooling an aspartame solution under conditions that prevent forced circulation in the crystallisation medium, is dried, after dewatering to a moisture content of less than 50%, to a moisture content of 2–6% in a continuous process using a pneumatic-conveyor dryer (as described in Perry's Chemical Engineer's Handbook, 6th edition, 1984 McGraw-Hill, pp. 20-51 to 20-54) and hot air of 80°–200° C. The dry product obtained is not granular though and would hence have to be subjected to an additional processing step to be converted into granular product. Moreover, as clearly specified in said patent application, this drying cannot be successfully carried out when aspartame that has crystallised from a solution via cooling with stirring is used as a starting product. See in particular the paragraph at the top of page 3 of EP-A-362706, which specifies that said starting product results in an end product of inferior quality owing to, in particular, adherence to the wall and decomposition.

The operation of pneumatic-conveyor dryers, as referred to in EP-A-362706, is based on the principle that the drying is effected exclusively via heat transfer between particles to be dried and the gas stream surrounding them, which subsequently absorbs the moisture. The residence time in such a pneumatic-conveyor dryer is only a few seconds, the conveyance being realized exclusively by the gas stream. In contrast to the drying in a pneumatic-conveyor dryer, the drying according to the process of the invention is realized through heat transfer via the wall of the dryer and simultaneous heat transfer with the gas stream.

The contact between the wet mass of crystals and the wall is mainly dependent on the speed of rotation and the shape of the paddles and can be represented by the Froude number. The Froude number must be higher than 1 and is preferably between 20 and 400.

The turbulent movement of the particles in the dryer according to the invention surprisingly leads to the formation of beautiful, more or less spherical granules of a uniform particle size.

Preferably, the wet mass of crystals is dried to a final moisture content of at most 38% because at higher moisture contents the granules are found to be less strong. For practical considerations the wet mass of crystals is dried to a moisture content of preferably 20–35% in the HSPD. Further drying is usually not critical because the granules obtained are strong enough for this. The further drying is preferably continued until a moisture content of less than 4% is obtained, in particular a moisture content of 2–3%. This further removal of moisture can very suitably be effected in the dryer used in the process according to the invention by adequately increasing the residence time in the dryer. However, it appears to be more advantageous to dry the already granular product having a moisture content of, preferably, at most 38% to a moisture content of less than 4% under suitable drying conditions in a second dryer of the same or any other type. If so desired, the further drying can also be effected in several dryers. When use is made of one or more afterdryers it is easy to optimise the productivity, drying conditions, prevention of product decomposition, etc.

The invention also covers the granulated product obtained, as shown in for example FIG. 1. The granulated aspartame obtainable with the process according to the invention differs from the granules according to the state of the art in for example its appearance. The granules obtained according to the invention are rounder. Because of this they appear to have surprisingly good properties: the granules produce very little dust during transportation and the granules have very good free-flowing properties.

The wet mass of aspartame crystals containing preferably 40–70% moisture may be obtained in many different ways. The wet mass of crystals may be the product obtained directly from an aspartame crystallisation process followed by a moisture-removal step such as filtration or centrifugation.

It is equally possible to supply powdery aspartame to the preferably separated product of an aspartame crystallisation process. Powdery aspartame is formed in the mechanical processing of aspartame and, as such, it is of less commercial value as it has a long dispersion time in water. It is hence a particular advantage that in the process according to the invention powdery aspartame can be used to produce well-dispersible granules.

In some cases it may be desirable to fractionate the product obtained from the drying step and to feed relatively small granules or crystals (for example of <200 m or <50 μm) back to the wet mass of crystals.

Preferably, the wet mass of aspartame crystals has a moisture content of 40–70%, in particular 42–64%. When for example aspartame powder or crystals with a moisture content of less than 40% are fed to the wet mass of crystals as described above, the moisture content of the wet mass of crystals must preferably remain above 40%.

It is a particular advantage that it is possible to obtain granular aspartame with a chosen and controllable average particle size and particle size distribution with the process according to the invention. The supply (flow rate and composition of the wet mass of crystals) is of minor importance in this respect. Of major importance is the positioning of the paddles. A person skilled in the art will be able to determine the optimum position in a few simple tests. It is for example advantageous for the distance between the wall and the paddles to be around 2 mm if a narrow particle size distribution is required. A greater distance will lead to a wider distribution. The position of the paddles affects the residence time and the turbulence. In general, it is advantageous to give a part of the paddles a negative pitch as this has been found to result in more effective drying. However, this may involve the drawback of a slightly greater degree of decomposition of the granules. The speed of rotation may be chosen within wide limits. A higher speed of rotation leads to better contact with the jacket and hence better drying. If the speed of rotation is too high, the forces exerted on the aspartame granules will be too strong and there will be a risk of the formation of a greater amount of fines.

In order to effect good drying within a short time, in which an unexpectedly small amount of decomposition appears to take place, the jacket of the HSPD has a temperature of 80°–190° C., preferably 100°–170° C., in particular 110°–140° C. In addition, the carrier gas has a temperature of 100°–200° C., preferably 140°–180° C. The humidity of the carrier gas is usually not critical. The carrier gas has a relative humidity at room temperature of, as a rule, less than 90%, preferably less than 70%.

The residence time of the aspartame in the paddle dryer is dependent on the positioning of the paddles, the speed of rotation of the paddles and the flow rate of the carrier gas. The carrier gas may optionally be passed through the HSPD countercurrently.

The residence time of the aspartame is about 15–600 seconds, preferably 20–180 seconds.

Under these circumstances, it unexpectedly appeared that micro-organisms were killed very effectively if aspartame with a moisture content of less than 35% preferably less than 10% was passed through the HSPD. Hence, the use of the HSPD for improving the microbiological characteristics of aspartame is claimed. By using the HSPD, it is unexpectedly easy to arrive at a microbiological contamination of less than 200, in particular less than 100, and even less than 20 microorganisms per gram.

The size of the granules obtained is generally between 50 μm and 1000 μm. It is also possible per se to produce dried aspartame with a smaller particle size with the aid of the HSPD but this is not preferable. Aspartame with a particle size of less than 20 μm is generally referred to as aspartame dust. This dust has relatively poor solubility properties because it disperses poorly in water. However, if aspartame with a particle size of less than 20 μm is desired, this can be produced in the HSPD without any difficulty, in particular by choosing a very high speed of rotation.

Particles of more than 900–1000 μm appear to dissolve in water relatively slowly and it is hence preferable to produce granules that include virtually no particles of more than 900 μm. Optionally, a screening step may be incorporated to remove unduly large particles.

A little aspartame dust may be formed in the various drying steps and the resultant granulate may contain particles with an undesired particle size. The dust is preferably removed from the completely dried aspartame (having a moisture content of 2–3%) and fed back to the wet mass of crystals. Granules with an undesired particle size can also be fed back. The granules are preferably between 100 and 800 μm. More in particular 80% of the particles are between 200 and 600 μm.

If they are dried to a moisture content of 2–3%, the aspartame granules obtained have a bulk density of 450–600 kg/m The aspartame granules are particularly suitable for use as a sweetener in the industrial production of sweetened drinks and the like as the aspartame disperses and dissolves relatively quickly in water, the granules have good free-flowing properties and little aspartame dust is formed during transportation and storage.

The invention will be further elucidated with reference to the following examples, without being limited thereto.

EXAMPLES I–IV

For the examples use was made of an ES 2050 Turbo Dryer from VOMM; the diameter of the turbine was 35.5 cm, the length was 2.5 m. Material was supplied with the aid of one or two feed screws. The product was collected, the fines being collected with the aid of a cyclone. The testing was done for a number of hours (2–4) using 50–60 kg/h of wet material.

Table I shows the details and results.

TABLE I

|  | Example | | | | |
| --- | --- | --- | --- | --- | --- |
|  | I | II | III* | IIIA** | IV* |
| % moisture in the feed | 60 | 61 | 54 | 11 | 61 |
| jacket temperature (°C.) | 90 | 90 | 110 | 110 | 110 |
| air temperature (°C.) | 150 | 160 | 190 | 190 | 190 |
| feed (kg/h) | 55 | 50 | 50 | 80 | 50 |
| air (m³/h) | 100 | 300 | 300 | 300 | 300 |
| rotor speed (rpm) | 700 | 700 | 850 | 600 | 900 |
| residence time (sec.) | 20 | 20 | 20 | 20 | 20 |
| % moisture in the product | 2.2 | 1.2 | 11 | 3 | 17 |
| bulk density (kg/m³) | 600 | 510 |  | 510 |  |
| % 250–500 µm | 42 | 51 |  |  |  |
| % 75–250 µm | 45 | 44 |  |  |  |
| % >500 µm | 10 | 3 |  |  |  |
| % <75 µm | 3 | 1 |  |  |  |
| d10 (µm) |  |  |  | 130 |  |
| d50 (µm) |  |  |  | 520 |  |
| d90 (µm) |  |  |  | 1040 |  |

*In examples III and IV granular product was also obtained.
**product of example III was used as the feed in example IIIA.

EXAMPLES V–IX

Experiments were carried out analogously to examples I–IV using two ES 450 Turbo Dryers from VOMM with diameters of 45.0 cm, which were connected in series. Table 2 shows the details and results. Powdery aspartame that was collected with the aid of a cyclone after the second drying step was added to the feed.

The first dryer was set as follows:

| speed of rotation | 700 rpm |
| --- | --- |
| jacket temperature | 100° C. |
| air supply | 1200 m³/h |
| air temperature | 128° C. | the second dryer as follows:

| speed of rotation | 560 rpm |
| --- | --- |
| jacket temperature | 115° C. |
| air supply | 700 m³/h |
| air temperature | 122° C. |

TABLE II

|  | Example | | | | |
| --- | --- | --- | --- | --- | --- |
|  | V | VI | VII | VIII | IX |
| initial moisture content (%) | 60 | 60 | 60 | 60 | 60 |
| % powder supplied | 20 | 15 | 10 | 5 | 0 |
| moisture content of feed (%) | 49 | 52 | 56 | 58 | 60 |
| feed (kg/h) | 110 | 104 | 120 | 96 | 80 |
| moisture after 1st step (%) | 26 | 30 | 32 | 34 | 34 |

TABLE II-continued

|  | Example | | | | |
| --- | --- | --- | --- | --- | --- |
|  | V | VI | VII | VIII | IX |
| moisture after 2nd step (%) | 2.2 | 2.4 | 2.3 | 2.5 | 2.6 |
| % >900 µm | 8 | 6 | 3 | 5 | 4 |
| % <180 µm | 5 | 6 | 9 | 8 | 9 |
| % between 180 and 900 µm | 87 | 88 | 88 | 87 | 87 |

EXAMPLES X–XIV

Tests were carried out analogously to examples V–IX, using aspartame containing 62% moisture, to which 20% powder was added, resulting in a wet mass of crystals containing 50.3% moisture; see Table 3.

The 1st dryer was set as follows:

| speed of rotation | 850 rpm |
| --- | --- |
| jacket temperature | variable (see Table 3) |
| air supply | 1200 m³/h |
| air temperature | variable (see Table 3) |

The second dryer was set as follows:

| speed of rotation | 560 rpm |
| --- | --- |
| jacket temperature | 140° C. |
| air supply | 700 m³/h |
| air temperature | 140° C. |

TABLE 3

|  | Example | | | | |
| --- | --- | --- | --- | --- | --- |
|  | X | XI | XII | XIII | XIV |
| feed (kg/h) | 123 | 144 | 144 | 194 | 194 |
| jacket temperature (°C.) | 110 | 110 | 120 | 120 | 130 |
| air temperature (°C.) | 140 | 140 | 150 | 150 | 160 |
| % moisture after 1st step | 23 | 28 | 24 | 30 | 26 |
| % >900 µm | 2 | 2 | 1 | 2 | 2 |
| % <180 µm | 8 | 10 | 12 | 13 | 14 |
| % between 180 and 900 µm | 90 | 88 | 87 | 83 | 84 |
| % moisture after 2nd step | 3.8 | 4.9 | 3.8 | 6.7 | 4.9 |
| % >900 µm | 1 | 1 | 1 | 1 | 1 |
| % <180 µm | 11 | 15 | 15 | 16 | 14 |
| % between 180 and 900 µm | 88 | 84 | 84 | 83 | 83 |

The granules obtained could be dried further in a fluidized-bed dryer without any difficulty.

EXAMPLES XV–XVI

Tests were carried out analogously to example X, which a third HSPD was used to obtain aspartame granules with a moisture content of less than 3%.

TABLE 4

|  | Example | |
| --- | --- | --- |
|  | XV | XVI |
| 1st dryer |  |  |
| % moisture in the feed (%) | 53 | 53 |
| feed (kg/h) | 310 | 310 |
| speed of rotation (rpm) | 850 | 850 |
| jacket temperature (°C.) | 150 | 150 |
| air supply (m³/h) | 1400 | 1400 |
| air temperature (°C.) | 172 | 172 |
| moisture content of the granules (%) | 32.5 | 32.5 |
| 2nd dryer |  |  |
| speed of rotation (rpm) | 420 | 420 |
| jacket temperature (°C.) | 140 | 140 |
| air supply (m³/h) | 700 | 750 |
| air temperature (°C.) | 151 | 151 |
| moisture content of the granules (%) | 13.5 | 13.5 |
| 3rd dryer |  |  |
| temperature of the feed (°C.) | 94 | 86 |
| speed of rotation (rpm) | 420 | 420 |
| jacket temperature (°C.) | 150 | 150 |
| air supply (m³/h) | 700 | 700 |

TABLE 4-continued

| | Example | |
|---|---|---|
| | XV | XVI |
| air temperature (°C.) | 151 | 151 |
| moisture content (%) | 0.9 | 1.6 |
| % >900 μm | 3 | 3 |
| % <180 μm | 20 | 24 |
| % between 900 and 180 μm | 77 | 73 |

EXAMPLE XVII

The drying of an aspartame wet cake with 51% moisture was carried out analogously to example XIV, and the amount of microorganisms were measured of a sample after the first and the second dryer. The moisture content of the granules after the first drying step was 30% after the second 11%.

Several tests were performed: =
total aerobic counts on Plate Count Agar (at 28° C. and 37° C.)
*Bacillus cereus* on Maunitol Egg Yolk Polymixine Agar
Pathogenic microorganisms on CLED medium
Staphylococcus species on Baird Parker medium.
All tests were performed according to standard analysis. The results (all in microorganism per g) are given in Table 5.

TABLE 5

| | Test method | | | | |
|---|---|---|---|---|---|
| | PCA 28° C. | PCA 37° C. | MEYP Agar | CLED medium | BP medium |
| first drying | >3.10$^4$ | >3.10$^3$ | neg | pos | pos |
| second drying | none | none | neg | neg | neg |

EXAMPLE XVIII

Aspartame, obtained commercially and left for 1 week in open cartons, appeared to contain 9% moisture and ~10$^6$ MO/g (PCA at 37° C.). After treatment in the HSPD as in the second step of example XIV, but with a rotor speed of 320 rpm the product contained 180 MO/g and 2.3% moisture.

We claim:

1. Process for drying and granulation of aspartame through the thermal treatment of a wet mass of aspartame crystals using a hot carrier gas, wherein the process comprises:
   supplying the wet mass of aspartame crystals, in a continuous process, to a high-speed paddle dryer fitted with a jacket heated to a temperature of 80°–190° C.;
   positioning paddles, mounted on a central shaft with a controllable speed of rotation, at an adjustable distance from and angle to the jacket, so as to provide more or less spherical granules of a narrow, controllable particle size distribution;
   rotating the shaft at a speed of rotation so as to produce a Froude number higher than 1;
   treating the wet mass of aspartame crystals in the paddle dryer for 15–600 seconds, with the simultaneous presence of a carrier gas having an inlet temperature of 100°–200° C.; and
   discharging a granular product from the paddle dryer.

2. Process as recited in claim 1, wherein the speed of rotation is chosen so that the Froude number is between 20 and 400.

3. Process as recited in claim 1, wherein the jacket of the paddle dryer has a temperature of 140°–180° C.

4. Process as recited in claim 1, wherein the carrier gas has a temperature of 140°–180° C.

5. Process as recited in claim 1 wherein the process includes a residence time of 20–180 seconds.

6. Process as recited in claim 1, wherein the wet mass of crystals is dried in the paddle dryer to a final moisture content of at most 38%.

7. Process as recited in claim 1, wherein the obtained granular product having a moisture content of at most 38% is dried further to a moisture content of less than 4%.

8. Process as recited in claim 1, wherein the wet mass of crystals with a moisture content of more than 40% is dried to a moisture content of 20–35%.

9. Process as recited in claim 1, wherein the granular product is dried further in the paddle dryer and optionally in an additional dryer.

10. Process as recited in claim 1, wherein the wet crystal mass is the product directly obtained from an aspartame crystallization process.

11. Process as recited in claim 1, wherein the wet mass of crystals is a mixture of wet aspartame crystals and powdery aspartame.

12. Process as recited in claim 1, wherein a portion of the product is fed back to the wet mass of crystals.

13. Process as recited in claim 12, wherein particles with dimensions of less than 50 μm are separated from the product and are fed back to the wet mass of crystals.

14. Granulated aspartame product produced by a process as recited in claim 1.

15. Method of using a high-speed paddle dryer fitted with a jacket heated to a temperature of 80°–190° C. and with paddles, mounted on a central shaft with a controllable speed of rotation, at an adjustment distance from and angle to the jacket, comprising the steps of:
   positioning the paddles so as to provide more or less spherical granules of a narrow, controllable particle size distribution;
   choosing the speed of rotation so as to produce a Froude number higher than 1; and
   passing aspartame with a moisture content of less than 35% with a carrier gas through the paddle dryer for decreasing the microbiological contamination of the aspartame.

16. Method of using a high-speed paddle dryer as recited in claim 15 for arriving at a microbiological contamination of less than 100 microorganisms per gram.

17. Process according to claim 1, wherein the granular product obtained is of the size between 50 μm and 1000 μm.

18. Process according to claim 1, wherein the granular product is further dried.

* * * * *